US006524626B2

(12) United States Patent
Chen

(10) Patent No.: US 6,524,626 B2
(45) Date of Patent: *Feb. 25, 2003

(54) GINSENG BERRY TOPICAL PRODUCTS

(75) Inventor: Jau-Fei Chen, Orem, UT (US)

(73) Assignee: E Excel International, Inc., Springville, UT (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,702

(22) Filed: Apr. 23, 1999

(65) Prior Publication Data

US 2002/0012644 A1 Jan. 31, 2002

(51) Int. Cl.⁷ ............................................. A61K 35/78
(52) U.S. Cl. ................................................... 424/728
(58) Field of Search .............................. 424/401, 195.1, 424/74, 728; 252/367.1; 425/74; 99/495, 510, 514

(56) References Cited

U.S. PATENT DOCUMENTS

| | | |
|---|---|---|
| 3,227,616 A | 1/1966 | Van Wessem |
| 4,042,720 A | 8/1977 | Forkner |
| 4,078,092 A | 3/1978 | Nishiyama .................. 426/584 |
| 4,276,890 A | 7/1981 | Fichera ........................ 131/270 |
| 4,361,554 A | 11/1982 | Saunders |
| 4,615,900 A | 10/1986 | Schenz et al. .............. 426/590 |
| 4,732,773 A | 3/1988 | Schott ......................... 426/590 |
| 4,737,367 A | 4/1988 | Langer et al. ................. 426/72 |
| 4,784,847 A | 11/1988 | Zulliger-Bopp et al. ...... 424/69 |
| 4,795,638 A | 1/1989 | Ayache et al. ............ 424/195.1 |
| 5,000,949 A | 3/1991 | Bias |
| 5,034,226 A | 7/1991 | Beck ....................... 424/195.1 |
| 5,171,577 A | 12/1992 | Griat et al. .................. 424/450 |
| 5,230,889 A | 7/1993 | Inoue ....................... 424/195.1 |
| 5,290,605 A | 3/1994 | Shapira ....................... 424/439 |
| 5,466,455 A | 11/1995 | Huffstutler, Jr. et al. .... 424/401 |
| 5,470,874 A | 11/1995 | Lerner ......................... 514/474 |
| 5,565,199 A | 10/1996 | Page et al. ................ 424/195.1 |
| 5,565,207 A | 10/1996 | Kashibuchi et al. ......... 424/401 |
| 5,571,503 A | 11/1996 | Mausner ....................... 424/59 |
| 5,578,312 A | 11/1996 | Parrinello |
| 5,595,743 A | 1/1997 | Wu .......................... 424/195.1 |
| 5,618,521 A | 4/1997 | de Rigal et al. .............. 424/59 |
| 5,643,587 A | 7/1997 | Scancarella et al. ......... 424/401 |
| 5,663,160 A | 9/1997 | Meybeck et al. ........... 514/182 |
| 5,665,365 A | 9/1997 | Bombardelli et al. ....... 424/401 |
| 5,676,956 A | 10/1997 | Duffy et al. ................. 424/401 |
| 5,676,958 A | 10/1997 | Emerson et al. |
| 5,720,962 A | 2/1998 | Ivy et al. ..................... 424/401 |
| 5,736,584 A | 4/1998 | Kunkel ........................ 514/919 |
| 5,738,887 A | 4/1998 | Wu ............................... 426/51 |
| 5,744,187 A | 4/1998 | Gaynor ....................... 426/599 |
| 5,747,462 A | 5/1998 | Fuentes ........................ 514/23 |
| 5,773,014 A | 6/1998 | Perrier et al. .............. 424/401 |
| 5,817,299 A | 10/1998 | Manirazman ................. 424/59 |
| 5,834,044 A | 11/1998 | Schmitz et al. ............... 426/73 |
| 5,840,309 A | 11/1998 | Herstein et al. ........... 424/195.1 |

FOREIGN PATENT DOCUMENTS

| | | |
|---|---|---|
| CN | 1048799 | 1/1991 |
| CN | 1076623 | 9/1993 |
| CN | 1076624 | 9/1993 |
| CN | 1076624 A | 9/1993 |
| CN | 1090988 A | 8/1994 |
| CN | 1097618 | 1/1995 |
| CN | 1103779 | 6/1995 |
| CN | 1114872 | 1/1996 |
| CN | 1120410 | 4/1996 |
| CN | 1125052 | 6/1996 |
| CN | 1133142 | 10/1996 |
| CN | 1211403 A | 3/1999 |
| DE | 27 03 189 A | 8/1978 |
| DE | 2703189 | 8/1978 |
| DE | 4331252 | 5/1994 |
| ES | 2 041 218 B | 5/1994 |
| FR | 2659014 | 9/1991 |
| JP | 51115968 | 10/1976 |
| JP | 52120154 | 10/1977 |
| JP | 52120154 A | 10/1977 |
| JP | 58067151 | 4/1983 |
| JP | 59227244 | 12/1984 |
| JP | 58 67151 | 4/1986 |
| JP | 61 85324 | 4/1986 |
| JP | 61092530 | 5/1986 |
| JP | 63 116669 | 5/1988 |
| JP | 63192705 | 8/1988 |
| JP | 5310527 | 11/1993 |
| JP | 6271452 | 9/1994 |
| JP | 7 267977 | 10/1995 |
| JP | 8332028 | 12/1996 |
| JP | 8333260 | 12/1996 |
| JP | 9 249576 | 9/1997 |
| KR | 97 032 503 A | 7/1997 |
| NL | 144830 | 2/1975 |
| WO | 93/11779 | 6/1993 |
| WO | 9507681 | 3/1995 |
| WO | 96 27383 A | 9/1996 |

OTHER PUBLICATIONS

Database CAPLUS on STN, AN 1987:633052, Bai et al., 'Study on dammarane–type saponins of ginseng fruit—isolation and identification of two configurational isomers,' Kexue Tongbao, 32(8):536–9, 1987.*

Database CAPLUS on STN, AN 1987:530921, Bai et al., 'Ginseng fruits—isolation and identification of saponins GF–II and GF–III,' Jilin Daxue Ziran Kexue Xuebao, (2):117–20, 1987.*

(List continued on next page.)

Primary Examiner—Russell Travers
Assistant Examiner—Alysia Berman
(74) Attorney, Agent, or Firm—Michael W. Starkweather; Brent T. Winder; Jones, Waldo, Holbrook & McDonough

(57) ABSTRACT

The present invention comprises novel combinations of ginseng berry juice and extracts combined with other skin nutrients and moisturizers which may be used to soften and moisturize the skin while providing essential vitamins and nutrients to the skin in a natural way.

9 Claims, No Drawings

OTHER PUBLICATIONS

Google internet search results, Feb. 2001.*
E. Excel Elemente Webpage, 1998.*
Database CAPLUS on STN, AN 1988:626950, JP 62273991 A2, Tsutsumi, T., Nov. 1978.*
Database CAPLUS on STN, AN 1984:435895, Matsuura et al., 'Further studies on dammarane–saponins of ginseng roots,' Chem. Pharm. Bull., 32(3):1188–92, 1984.*
Database CAPLUS on STN, AN 1982:578707, Besso et al., 'Ginsenoside–Ra1 and ginsenoside–Ra2, new dammarane––saponins of ginseng roots,' Chem. Pharm. Bull., 30(7):2380–5, 1982.*
Database CAPLUS on STN, AN 1978:412034, Pleinard et al., 'Testing of Panaz ginseng C. A. Meyer,' Ann. Pharm. Fr., 35(11–12):465–73, 1977.*
Chemical Abstracts AN 128:2008808 of JP 10072338, Lee, Sang Shung, 1998.*
Database CAPLUS on STN, AN 1994:38051, Liu et al., 'Preparation of ginseng fruit ginsenoside oral liquids', abstract and key words, Zhongguo Yaoxue Zazhi, 28(9):541–2, 1993.*
Database CAPLUS on STN, AN 1993:513413, Zhao et al., 'Chemical constituents of the fruit of Panax ginseng C.A. Meyer', abstract and key words, Zhongguo Zhongyao Zazhi, 18(5):296–7, 1993.*
Database CAPLUS on STN, AN 1992:466553, Zhao et al., 'Isolation and identification of 20®–gnsenoside–Rh2 (an anticancer constituent) from the fruits of Panax ginseng C.A. Meyer', abstract and key words, Zhongguo Zhongyao Zazhi, 16(11):678–9, 1991.*
Database CAPLUS on STN, AN 1988:470393, Bai et al., 'Study on ginseng fruits—identification of the saponins GF–I, GF–IV and GF–V,' abstract and key words, Kexue Tongbao, 33(5):379–81, 1988.*
English translation of CN 1194104A (Wang et al.), Sep. 1998.*
English translation of CN 87100825A (Wu), Aug. 1988.*
English translation of CN 1070575 A (Ma et al.), Apr. 1993.*
Derwent Abstracts, week 199645, AN 1996–453445, RU 2053272 C1 (Artyukov et al.), Jan. 1996.*
Derwent Abstracts, week 199821, AN 1998–238295, RU 2091469 C1 (Artyulov et al.), Sep. 1997.*
Database Derwent on West, week 197905, AN 1979–08268B, DE 2732749 A (Salome), Jan. 1979.*
Database Derwent on West, week 199019, AN 1990–140136, CN 1033278 A (Fei et al.), Jun. 1989.*
English language abstract for Chinese Patent No. 1125052, Jun. 1996.
English language abstract for Chinese Patent No. 1120410, Apr. 1996.
English language abstract for Chinese Patent No. 1076624, Sep. 1993.
English language abstract for Chinese Patent No. 1076623, Sep. 1993.
English language abstract for Chinese Patent NO. 1048799, Jan. 1991.
English language abstract for Japanese Patent 5310527, Nov. 1993.
English language abstract for Japanese Patent No. 6271452, Sep. 1994.
English language abstract for Japanese Patent No. 8332028, Dec. 1996.
English language abstract for Japanese Patent No. 63192705, Oct. 1988.
English language abstract for Japanese Patent No. 61092530, May 1986.
English language abstract for Japanese Patent No. 59227244, Dec. 1984.
English language abstract for Japanese Patent No. 58067151, Apr. 1983.
English language abstract for Chinese Patent No. 1133142, Oct. 1996.
English language abstract for Chinese Patent No. 1114872, Jan. 1996.
English language abstract for Chinese Patent No. 1103779, Jun. 1995.
English language abstract for Chinese Patent No. 1097618, Jan. 1995.
English language abstract for Japanese Patent No. 8333260, Dec. 1996.
English language abstract for Japanese Patent No. 6271452, Sep. 1994.
English language abstract for German Patent No. 4331252, May 1994.
English language abstract for French Patent No. 2659014, Sep. 1991.
English language abstract for German Patent No. 2703189, Aug. 1978.
English language abstract for Japanese Patent No. 52120154, Oct. 1997.
English language abstract for Japanese Patent No. 51115968, Oct. 1976.
English language abstract for Netherlands Patent No. 144830, Feb. 1975.
XP–002142524, AN 1966–03816F, Murray, E.P., PN ZA 6000062 A, no publication date.
English language abstract for Japanese Patent No. 52120154A, Derwent WPI on Dialog. AN 77–82194y/197746, Shizuoka–Prefecture (SHIZ–N), Oct. 8, 1977.
Patent application No. 934523, South Africa, Karsten, K.A., 'Medicinal Preparation' No publication date.

* cited by examiner

GINSENG BERRY TOPICAL PRODUCTS

RELATED APPLICATIONS

The following applications are being filed concurrently herewith on this 23$^{rd}$ day of April 1999 and are incorporated herein by reference:

| Title | Atty Docket No. | Express Mailing Label Nos. |
|---|---|---|
| Cactus Fruit Skin Care Products | 7537.0029 | EL 113 362 519 US |
| Cactus Fruit Drinks and Food Products | 7537.0026 | EL 113 362 479 US |
| Ginseng Berry Drink and Food Compositions | 7537.0028 | EL 113 362 482 US |
| Ginseng Berry Powder Dietary Supplements | 7537.0030 | EL 113 362 496 US |
| Cactus Fruit Powder Dietary Supplements | 7537.0031 | EL 113 362 465 US |

FIELD OF THE INVENTION

The present invention relates generally to the field of skin care products and more particularly to products and methods which deliver fresh vitamins and other nutrients to the skin by topical application of a novel, vitamin-rich fruit composition. The present invention comprises ginseng berry extract and other skin nutrients and, preferably, other skin nutrients and moisturizers which are beneficial to the skin.

BACKGROUND

Human skin is extremely susceptible to the temperature and humidity extremes of our environment. However, when skin care products are properly used to counteract adverse environmental conditions, skin can remain healthy and beautiful under a variety of extreme environmental conditions. The environmental factors that most often affect the skin adversely are ultraviolet radiation and humidity.

Ultraviolet radiation varies with time of day, from day to night, with seasons of the year and weather conditions. The geographic region where one lives and the climate will also affect the amount of radiation to which one's skin is exposed. The sun's rays can dry skin through direct moisture loss or through the effects of radiation on the skin which may cause tanning and burning as well as moisture loss.

Skin may also face adverse conditions in the workplace where excessive temperatures or low humidity may harm skin. Exposure to chemicals may also remove moisture from the skin causing damage and actual skin chafing and loss if not treated properly.

Consequently, a mild skin moisturizer that nourishes the skin with natural ingredients and that can be repeatedly applied to the skin is beneficial in areas where skin is particularly susceptible to environmental damage.

In addition to environmental factors, skin must also be properly nourished. Maintaining healthy skin requires maintenance of proper moisture in the skin as well as delivery of essential vitamins to the skin. Vitamins may be consumed in the diet or may be applied directly to the skin.

For some people, oral consumption of vitamin C, especially in large doses, can have detrimental side effects ranging from mouth irritation to overdose. Yet large doses are sometimes considered beneficial to provide the skin with an effective amount of vitamin C. Vitamin C promotes collagen synthesis through its free radical scavenging attributes and its enzyme reactions which, in turn, promotes wound healing and skin health. Vitamin C is also toxic to many cancer cells including melanoma and has been found to catalyze the immune reaction to viral and bacterial infections.

Natural skin care products and remedies are popular among health-conscious consumers today. Many people prefer to enhance their appearance and health with vitamins and other nutrients in a "natural" way from naturally occurring sources. "Natural" products including natural vitamins are now in high demand. These are vitamins which are found in a product in its natural state without vitamin supplements or vitamin "fortification." While fruit and vegetable juices are known to have high concentrations of vitamins in their natural state and are often a preferred source of vitamins for internal consumption, many natural fruit and vegetable products are largely overlooked as a topical skin application.

What is needed is a skin care product and method that delivers natural vitamins, nutrients and other beneficial products to the skin without oral consumption and its adverse side-effects. Also needed is a natural product which can moisturize as well as nourish the skin.

SUMMARY AND OBJECTS OF THE INVENTION

Accordingly, it is an object of the present invention to provide a product and method which can deliver natural vitamins, skin nutrients and skin protectants to the skin in a topical application that nourishes and moisturizes the skin naturally.

The present invention comprises novel compositions of extracts from ginseng berry, herbs and preferably also other skin care ingredients which are mixed to form a topical application.

It is an object of preferred embodiments of the present invention to deliver natural vitamins to the skin.

It is another object of preferred embodiments of the present invention to deliver natural fruit and vegetable extracts to the skin so that the skin may benefit from natural vitamins, emollients and other healthful ingredients.

It is yet another object of preferred embodiments of the present invention to deliver natural and healthful herbs to the skin.

It is a further object of preferred embodiments of the present invention to moisturize the skin.

DETAILED DESCRIPTION OF THE PREFERRED EMBODIMENTS

The present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

The present invention is directed towards skin care products and topical skin products containing juice from the ginseng berry. Although the ginseng root is sometimes used as an herbal supplement, the ginseng berry has been overlooked due, at least in part, to its high seed content. Ginseng berries contain a large number of seeds which make up a large percentage of the berry's volume. These seeds must be removed in order to make a liquid suitable for use in topical skin applications.

Laboratory analysis of the juice from ginseng berries used for preferred embodiments of the skin care products of the present invention shows a high concentration of essential vitamins. The following Table 1 gives the result of a laboratory analysis of the essential vitamins and ingredients found in ginseng berry juice.

TABLE 1

| | |
|---|---|
| Riboflavin | 171.9 ug/gram of product |
| Vitamin A | 109 IU |
| Vitamin E | 1.5 IU |
| Beta Carotene | 16.9 IU |

Advantageously, ginseng berry juice also acts as an antioxidant. Laboratory analysis reveals that one gram of ginseng berry contains 1.4 times more antioxidant that 10 mg of Vitamin C.

Modern machinery may be used to produce juice from ginseng berries, however one presently preferred method of the present invention comprises a manual process. In this process, whole ginseng berries are crushed in a press thereby removing the majority of the juice. The seeds are then removed from the juice by filtration through a coarse screen filter. When a solids-free liquid is desired, the juice is further filtered in a 0.2 micron micro-filtration system to remove even finer solids. Some solids content may be acceptable or desired to improve texture or add fiber to the final product. When this is the case, the micro-filtration step may be omitted.

After the juice has been extracted, it is preferably blended with other natural ingredients which may add moisturizing effects, provide UV protection, or provide other physiological benefits.

Application of natural herb products along with the beneficial vitamins contained in ginseng berry juice may also increase health and vitality. The effects of various herbs and plant products are beneficial to the nervous, digestive and circulatory systems as well as other physiological functions. Herbs which, when applied to the skin, are beneficial to one's health and vitality may be considered to be "natural skin supplements." The combination of herbal ingredients with healthful and rejuvenating ginseng berry juice products offers the health advantages of natural vitamins and herbs in an aromatic, pleasing and healthful skin application.

Ginseng root also has beneficial physiological effects. It is believed to help regulate blood pressure and increase the body's resistance to adverse physical, chemical and biological influences. Ginseng root can stimulate physical and mental activity and protect against the adverse effects of mental and physical stress. It may also improve concentration and stimulate brain cells. Ginseng root may be considered to be an herbal stimulant.

Ginseng root also has beneficial physiological effects. It is believed to help regulate blood pressure and increase the body's resistance to adverse physical, chemical and biological influences. Ginseng root can stimulate physical and mental activity and protect against the adverse effects of mental and physical stress. It may also improve concentration and stimulate brain cells. Ginseng root may be considered to be a natural skin supplement. In the prior art, like some vitamins, ginseng root is often offered in capsules or tablets in a raw form. This can be difficult for some to ingest due to gag reflexes, physical impairment or psychological aversion to tablet or capsule consumption. A topical skin application allows a user to benefit from many of the beneficial effects of ginseng root without the requirement of ingesting the substance.

Preferred embodiments of the present invention combine the juice of ginseng berries with herbal supplements and stimulants and/or other natural skin supplements to create an application that has pleasurable sensory effect on the user and which provides a great variety of ingredients essential to health and vitality.

Other products within the scope of the present invention may be created from ginseng berry juice. Ginseng berry juice may be concentrated by known techniques to form a concentrated extract or syrup. This concentration may be performed on the pure juice of the ginseng berry or it may be performed after mixing the juice with natural skin supplements or other ingredients. The concentrated extract or syrup may then be diluted with water to return it to a juice state as needed. When more fiber or texture is desired, the final filtration step of the juice making process using a 0.2 micron filter may be omitted or replaced with a step which utilizes a coarser filter. Alternatively, fiber and texture producing ingredients may be added as needed.

The novel method and composition of the present invention allows users to apply natural vitamins, anti-oxidants and emollients directly to the skin.

The following tables further illustrate the ingredients currently used in the certain presently preferred embodiments. Ingrdients listed in these tables are given by weight percentage of the total mixture.

EXAMPLE 1

| Replenishing Masque for Dry Skin | |
|---|---|
| Ginseng (*Panax Ginseng*) Berry Extract | 11% |
| Water | 28.9% |
| SD Alcohol 40B | 10% |
| Glycerin | 7% |
| Hybrid Sunflower (*Helianthus Annuus*) Oil | 6% |
| Polyacrylamide | 5% |
| C13-14 Isoparaffin | 5% |
| Laureth-7 | 5% |
| Cyclomethicone | 5% |
| Grape (*Vitis Vinifera*) Seed Extract | 3% |
| Ginseng (*Panax Ginseng*) Root Extract | 2% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Flowery Knotweed (*Polygonum Aviculare*) | 1% |
| *Hibiscus Sabdariff* | 1% |
| Mulberry (*Morus Alba*) Leaf | 1% |
| Riboflavin (Vitamin B2) | 1% |
| Tocopheryl Acetate (Vitamin E Acetate) | 1% |
| Niacin (Vitamin B3) | 1% |
| Pantothenic Acid (Provitamin B5) | 1% |
| Disodium Edta | 0.1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 2

| Intensive Night Repair | |
|---|---|
| Ginseng (*Panax Ginseng*) Berry Extract | 12% |
| Water | 33.9% |
| Shea Butter (*Butyrospermum Parkii*) | 4.5% |
| Glycerin | 4.5% |
| Cyclomethicone | 4.5% |
| Isopropyl Palmitate | 4% |
| Glyceryl Stearate | 4% |
| Stearic Acid | 4% |
| Sodium Behenoyl Lactylate | 4% |
| Grape (*Vitis Vinifera*) Seed Extract | 4% |
| Ginseng (*Panax Ginseng*) Root Extract | 4% |
| Avocado (*Persea Gratissima*) | 2% |
| Cucumber (*Cucumis Sativus*) | 2% |
| Jasmine (*Jasminum Officinale*) | 2% |
| Orange (*Citrus Aurantium Dulcis*) Peel | 2% |

-continued

| Intensive Night Repair | |
|---|---|
| Flowery Knotweed (*Polygonum Aviculare*) | 1% |
| *Hibiscus Sabdariff* | 1% |
| Mulberry (*Morus Alba*) Leaf | 1% |
| Pyridoxine (Vitamin B6) | 1% |
| Riboflavin (Vitamin B2) | 1% |
| Tocopheryl Acetate (Vitamin E Acetate) | 1% |
| Pantothenic Acid (Provitamin B5) | 1% |
| Xanthan Gum | 0.2% |
| Carbomer | 0.2% |
| Disodium Edta | 0.2% |
| Phenoxyethanol | 0.2% |
| Methylparaben | 0.2% |
| Butylparaben | 0.2% |
| Ethylparaben | 0.2% |
| Propylparaben | 0.2% |
| Triethanolamine | 0.2% |

EXAMPLE 3

| Revitalizing Facial Cleanser | |
|---|---|
| Ginseng (*Panax Ginseng*) Berry Extract | 9% |
| Water | 54.5% |
| Sodium Cocoyl Isethionate | 5% |
| Sodium Methyl Cocoyl Taurate | 4% |
| PEG-8 | 4% |
| Octyldodecyl Benzoate | 3.5% |
| Myristic Acid | 3% |
| Glyceryl Stearate SE | 3% |
| Ginseng (*Panax Ginseng*) Root Extract | 3% |
| *Chrysanthemum Coccineum* | 1% |
| Cucumber (*Cucumis Sativus*) | 1% |
| Sage (*Salvia Officinalis*) | 1% |
| Grapefruit (*Citrus Grandis*) Peel | 1% |
| Kiwi (*Actinidia Chinensis*) | 1% |
| Lemon (*Citrus Medica LI*) | 1% |
| Algae | 1% |
| White Water Lily (*Nymphaea Alba*) | 1% |
| Niacin (Vitamin B3) | 1% |
| Tocopheryl Acetate (Vitamin E Acetate) | 1% |
| Butylene Glycol | 0.2% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 4

| All-Day Hydrating Nourisher | |
|---|---|
| Ginseng (*Panax Ginseng*) Berry Extract | 9% |
| Water | 53% |
| Shea Butter (*Butyrospermum Parkii*) | 3.5% |
| Glycerin | 3.5% |
| Cyclomethicone | 3.5% |
| Glyceryl Stearate | 3% |
| Stearic Acid | 3% |
| Sodium Behenoyl Lactylate | 3% |
| Grape (*Vitis Vinifera*) Seed Extract | 3% |
| Ginseng (*Panax Ginseng*) Root Extract | 3% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Flowery Knotweed (*Polygonum Aviculare*) | 1% |
| *Hibiscus Sabdariff* | 1% |

-continued

| All-Day Hydrating Nourisher | |
|---|---|
| Mulberry (*Morus Alba*) Leaf | 1% |
| Pyridoxine (Vitamin B6) | 1% |
| Riboflavin (Vitamin B2) | 1% |
| Tocopheryl Acetate (Vitamin E Acetate) | 1% |
| Pantothenic Acid (Provitamin B5) | 1% |
| Xanthan Gum | 0.2% |
| Carbomer | 0.2% |
| Disodium Edta | 0.1% |
| Phenoxyethanol | 0.2% |
| Methylparaben | 0.2% |
| Butylparaben | 0.2% |
| Ethylparaben | 0.2% |
| Propylparaben | 0.2% |
| Triethanolamine | 0.2% |

EXAMPLE 5

| Time Signature Pure Ginseng Masque | |
|---|---|
| Ginseng (*Panax Ginseng*) Berry Extract | 62.9% |
| Ginseng (*Panax Ginseng*) Root Extract | 5% |
| SD Alcohol 40B | 3% |
| Glycerin | 3% |
| Hybrid Sunflower (*Helianthus Annuus*) Oil | 2% |
| Polyacrylamide | 2% |
| C13-14 Isoparaffin | 2% |
| Laureth-7 | 2% |
| Cyclomethicone | 2% |
| Avocado (*Persea Gratissima*) | 2% |
| Cucumber (*Cucumis Sativus*) | 2% |
| Jasmine (*Jasminum Officinale*) | 2% |
| Orange (*Citrus Aurantium Dulcis*) Peel | 2% |
| Flowery Knotweed (*Polygonum Aviculare*) | 1% |
| *Hibiscus Sabdariff* | 1% |
| Mulberry (*Morus Alba*) Leaf | 1% |
| Riboflavin (Vitamin B2) | 1% |
| Tocopheryl Acetate (Vitamin E Acetate) | 1% |
| Niacin (Vitamin B3) | 1% |
| Pantothenic Acid (Provitamin B5) | 1% |
| Disodium Edta | 0.1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 6

| Replenishing Masque for Normal Skin | |
|---|---|
| Ginseng (*Panax Ginseng*) Berry Extract | 10% |
| Water | 39.9% |
| Glycerin | 5% |
| Cyclomethicone | 5% |
| Polyacrylamide | 5% |
| C13-14 Isoparaffin | 5% |
| Laureth-7 | 5% |
| Aluminum Starch Octenylsuccinate | 5% |
| Hybrid Sunflower (*Helianthus Annuus*) Oil | 5% |
| Grape (*Vitis Vinifera*) Seed Extract | 2% |
| Ginseng (*Panax Ginseng*) Root Extract | 1% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Flowery Knotweed (*Polygonum Aviculare*) | 1% |
| *Hibiscus Sabdariff* | 1% |

-continued

| Replenishing Masque for Normal Skin | |
|---|---|
| Mulberry (*Morus Alba*) Leaf | 1% |
| Riboflavin (Vitamin B2) | 1% |
| Tocopheryl Acetate (Vitamin E Acetate) | 1% |
| Niacin (Vitamin B3) | 1% |
| Pantothenic Acid (Provitamin B5) | 1% |
| Disodium Edta | 0.1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 7

| Deep Purifying Clay Masque | |
|---|---|
| Ginseng (*Panax Ginseng*) Berry Extract | 6.5% |
| Water | 57.5% |
| Kaolin | 7% |
| Glycerin | 5% |
| Glyceryl Stearate SE | 5% |
| Bentonite | 3% |
| Ginseng (*Panax Ginseng*) Root Extract | 3% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Flowery Knotweed (*Polygonum Aviculare*) | 1% |
| Hibiscus Sabdariff | 1% |
| Mulberry (*Morus Alba*) Leaf | 1% |
| Riboflavin (Vitamin B2) | 1% |
| Tocopheryl Acetate (Vitamin E Acetate) | 1% |
| Niacin (Vitamin B3) | 1% |
| Pantothenic Acid (Provitamin B5) | 1% |
| Magnesium Aluminum Silicate | 1% |
| Phenoxyethanol | 0.2% |
| Methylparaben | 0.2% |
| Ethylparaben | 0.2% |
| Propylparaben | 0.2% |
| Disodium Edta | 0.2% |

EXAMPLE 8

| Advanced Spot Control | |
|---|---|
| Ginseng (*Panax Ginseng*) Berry Extract | 11% |
| Water | 61.4% |
| SD Alcohol 40B | 7% |
| Glycerin | 5% |
| Grape (*Vitis Vinifera*) Seed Extract | 2% |
| Ginseng (*Panax Ginseng*) Root Extract | 2% |
| Chrysanthemum Coccineum | 1% |
| Cucumber (*Cucumis Sativus*) | 1% |
| Sage (*Salvia Officinalis*) | 1% |
| Grapefruit (*Citrus Grandis*) Peel | 1% |
| Kiwi (*Actinidia Chinensis*) | 1% |
| Lemon (*Citrus Medica Limonum*) | 1% |
| Orange (*Citrus Aurantium Dulcis*) Peel | 1% |
| Niacin (Vitamin B3) | 1% |
| Folic Acid | 1% |
| Tocopheryl Acetate (Vitamin E Acetate) | 1% |
| Triclosan | 1% |
| Carbomer | 0.3% |
| Triethanolamine | 0.3% |

EXAMPLE 9

| Intensive Day Defense | |
|---|---|
| Ginseng (*Panax Ginseng*) Berry Extract | 5% |
| Water | 40.5% |
| Octyl Methoxycinnamate | 2% |
| Oxybenzone | 2% |
| Avobenzone | 2% |
| Phenylbenzimidazole Sulfonic Acid | 2% |
| Aloe Barbadensis Gel | 4% |
| Glycerin | 4% |
| Octyl Stearate | 3% |
| C12–15 Alkyl Bezoate | 3% |
| Stearic Acid | 3% |
| Glyceryl Stearate | 3% |
| Isopropyl Palmitate | 2.5% |
| Octocrylene | 2% |
| Sodium Stearoyl Lactylate | 2% |
| Grape (*Vitis Vinifera*) Seed Extract | 2% |
| Ginseng (*Panax Ginseng*) Root Extract | 2% |
| Avocado (*Persea Gratissima*) | 1% |
| Cucumber (*Cucumis Sativus*) | 1% |
| Jasmine (*Jasminum Officinale*) | 1% |
| Pyridoxine (Vitamin B6) | 1% |
| Riboflavin (Vitamin B2) | 1% |
| Tocopheryl Acetate (Vitamin E Acetate) | 1% |
| Ascorbic Acid (Vitamin C) | 1% |
| Niacin (Vitamin B3) | 1% |
| Triethanolamine | 1% |
| Potassium Hydroxide | 1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 10

| Body Wash | |
|---|---|
| Ginseng (*Panax Ginseng*) Berry Extract | 5% |
| Water | 48% |
| Decyl Glucoside | 6% |
| Aloe Barbadensis Gel | 6% |
| PEG-120 Methyl Glucose Dioleate | 6% |
| Ammonium Laureth Sulfate | 5% |
| Disodium Cocoamphodiacetate | 4% |
| Grape (*Vitis Vinifera*) Seed Extract | 1% |
| Chrysanthemum Coccineum | 1% |
| Cucumber (*Cucumis Sativus*) Sage | 1% |
| Kiwi (*Actinidia Chinensis*) | 1% |
| Lemon (*Citrus Medica Limonum*) | 1% |
| Rose (*Rosa Damascena*) | 1% |
| White Water Lily (*Nymphaea Alba*) | 1% |
| Riboflavin (Vitamin B2) | 1% |
| Tocopheryl Acetate (Vitamin E Acetate) | 1% |
| PEG-7 Glyceryl Cocoate | 1% |
| Cocamidopropyl Betaine | 1% |
| Fragrance | 0.2% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 11

| Hydrating Exfoliant | |
|---|---|
| Ginseng (*Panax Ginseng*) Berry Extract | 9% |
| Water | 44.5% |
| Disodium Laureth Sulfosuccinate | 6% |
| Polyethylene | 5% |
| Glycerin | 5% |
| Cocamidopropyl Betaine | 4.5% |
| Peg-120 Methyl Glucose Dioleate | 4% |
| Triethanolamine | 4% |
| Ginseng (*Panax Ginseng*) Root Extract | 3% |
| Grape (*Vitis Vinifera*) Seed Extract | 2% |
| Chrysanthemum Coccineum | 1% |
| Cucumber (*Cucumis Sativus*) | 1% |
| Sage (*Salvia Officinalis*) | 1% |
| Grapefruit (*Citrus Grandis*) Peel | 1% |
| Kiwi (*Actinidia Chinensis*) | 1% |
| Lemon (*Citrus Medica Limonum*) | 1% |
| Rose (*Rosa Damascena*) | 1% |
| Algae | 1% |
| White Water Lily (*Nymphaea Alba*) | 1% |
| Niacin (Vitamin B3) | 1% |
| Tocopheryl Acetate (Vitamin E Acetate) | 1% |
| Polysorbate 20 | 1% |
| Benzophenone-4 | 0.2% |
| Phenoxyethanol | 0.2% |
| Methylparaben | 0.2% |
| Butylparaben | 0.2% |
| Ethylparaben | 0.2% |
| Propylparaben | 0.2% |
| Carbomer | 0.2% |
| Disodium Edta | 0.2% |

EXAMPLE 12

| Hair Conditioner | |
|---|---|
| Ginseng (*Panax Ginseng*) Berry Extract | 9% |
| Water | 47% |
| Isopropyl Palmitate | 6% |
| Behentrimonium Methosulfate | 6% |
| Grape (*Vitis Vinifera*) Seed Extract | 3% |
| Cactus (*Cereus Gradiflorus*) Stem | 2% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Chrysanthemum Coccineum | 1% |
| Pantothenic Acid (Provitamin B5) | 1% |
| Phytantriol | 1% |
| Folic Acid | 1% |
| Biotin (Vitamin H) | 1% |
| PG-Hydroxyethylcellulose Cocodimonium Chloride | 1% |
| Tridecyl Stearate | 1% |
| Neopentyl Glycol Disaprylate | 1% |
| Tridecyl Trimellitate | 1% |
| Silk Amino Acids | 1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 13

| All-Day Hydrating Nourisher for Oily Skin | |
|---|---|
| Ginseng (*Panax Ginseng*) Berry Extract | 10% |
| Water | 52.8% |
| Glycerin | 5% |
| Cyclomethicone | 5% |
| Polyacrylamide | 4% |
| C13–14 Isoparaffin | 4% |
| Laureth-7 | 4% |
| Grape (*Vitis Vinifera*) Seed Extract | 2% |
| Ginseng (*Panax Ginseng*) Root Extract | 2% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Flowery Knotweed (*Polygonum Aviculare*) | 1% |
| Hibiscus Sabdariff | 1% |
| Tocopheryl Acetate (Vitamin E Acetate) | 1% |
| Ascorbic Acid (Vitamin C) | 1% |
| Folic Acid | 1% |
| Acrylates Copolymer | 0.5% |
| Isopropyl Palmitate | 0.5% |
| Disodium Edta | 0.2% |
| Phenoxyethanol | 0.2% |
| Methylparaben | 0.2% |
| Butlyparaben | 0.2% |
| Ethylparaben | 0.2% |
| Propylparaben | 0.2% |
| Carbomer | 0.2% |
| Triethanolamine | 0.2% |

EXAMPLE 14

| Time Signature, Ginseng Essence | |
|---|---|
| Ginseng (*Panax Ginseng*) Berry Extract | 60.3% |
| Ginseng (*Panax Ginseng*) Root Extract Extract | 8% |
| Grape (*Vitis Vinifera*) Seed Extract | 3% |
| Shea Butter (*Butyrospermum Parkii*) | 3% |
| Glycerin | 3% |
| Cyclomethicone | 3% |
| Isopropyl Palmitate | 2% |
| Glyceryl Stearate | 2% |
| Stearic Acid | 2% |
| Sodium Behenoyl Lactylate | 1% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Flowery Knotweed (*Polygonum Aviculare*) | 1% |
| Hibiscus Sabdariff | 1% |
| Mulberry (*Morus Alba*) Leaf | 1% |
| Pyridoxine (vitamin B6) | 1% |
| Riboflavin (Vitamin B2) | 1% |
| Tocopheryl Acetate (Vitamin E Acetate) | 1% |
| Pantothenic Acid (Provitamin B5) | 1% |
| Xanthan Gum | 0.3% |
| Carbomer | 0.3% |
| Disodium Edta | 0.1% |
| Phenoxyethanol | 0.2% |
| Methylparaben | 0.2% |
| Butlyparaben | 0.2% |
| Ethylparaben | 0.2% |
| Propylparaben | 0.2% |
| Triethanolamine | 0.2% |

EXAMPLE 15

| Tooth Paste: | |
| --- | --- |
| Ginseng (*Panax Ginseng*) Berry Extract | 4% |
| Stevia | 25% |
| Deionized Water | 23.6% |
| Hydrated Silica | 20% |
| Sorbitol | 18% |
| Ginseng | 4% |
| Sodium Lauroyl Sarcosinate | 1.5% |
| Flavor | 1% |
| PEG-6 | 0.8% |
| Tetrasodium Pyrophosphate | 0.5% |
| Cellulose gum | 0.5% |
| Sodium Benzoate | 0.5% |
| Triclosan | 0.3% |
| Hydrogen Peroxide | 0.3% of 35% actives |

EXAMPLE 16

| Revitalizing Facial Cleanser | |
| --- | --- |
| Ginseng (*Panax Ginseng*) Berry Extract | 3% |
| Cactus (*Cereus Grandiflorus*) | 3% |
| Cactus (*Cereus Grandiflorus*) Fruit | 3% |
| Water | 54.5% |
| Sodium Cocoyl Isethionate | 5% |
| Sodium Methyl Cocoyl Taurate | 4% |
| PEG-8 | 4% |
| Octyldodecyl Benzoate | 3.5% |
| Myristic Acid | 3% |
| Glyceryl Stearate SE | 3% |
| Ginseng (*Panax Ginseng*) Root Extract | 3% |
| Chrysanthemum Coccineum | 1% |
| Cucumber (*Cucumis Sativus*) | 1% |
| Sage (*Salvia Officinalis*) | 1% |
| Grapefruit (*Citrus Grandis*) Peel | 1% |
| Kiwi (*Actinidia Chinensis*) | 1% |
| Lemon (*Citrus Medica LI*) | 1% |
| Algae | 1% |
| White Water Lily (*Nymphaea Alba*) | 1% |
| Niacin (Vitamin B3) | 1% |
| Tocopheryl Acetate (Vitamin E Acetate) | 1% |
| Butylene Glycol | 0.2% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 17

| All-Day Hydrating Nourisher | |
| --- | --- |
| Ginseng (*Panax Ginseng*) Berry Extract | 3% |
| Cactus (*Cereus Grandiflorus*) Extract | 3% |
| Cactus (*Cereus Grandiflorus*) Fruit Extract | 3% |
| Water | 53% |
| Shea Butter (*Butyrospermum Parkii*) | 3.5% |
| Glycerin | 3.5% |
| Cyclomethicone | 3.5% |
| Glyceryl Stearate | 3% |
| Stearic Acid | 3% |
| Sodium Behenoyl Lactylate | 3% |
| Grape (*Vitis Vinifera*) Seed Extract | 3% |
| Ginseng (*Panax Ginseng*) Root Extract | 3% |
| Avocado (*Persea Gratissima*) | 1% |
| Cucumber (*Cucumis Sativus*) | 1% |
| Jasmine (*Jasminum Officinale*) | 1% |

| All-Day Hydrating Nourisher -continued | |
| --- | --- |
| Orange (*Citrus Aurantium Dulcis*) Peel | 1% |
| Flowery Knotweed (*Polygonum Aviculare*) | 1% |
| Hibiscus Sabdariff | 1% |
| Mulberry (*Morus Alba*) Leaf | 1% |
| Pyridoxine (Vitamin B6) | 1% |
| Riboflavin (Vitamin B2) | 1% |
| Tocopheryl Acetate (Vitamin E Acetate) | 1% |
| Pantothenic Acid (Provitamin B5) | 1% |
| Xanthan Gum | 0.2% |
| Carbomer | 0.2% |
| Disodium Edta | 0.1% |
| Phenoxyethanol | 0.2% |
| Methylparaben | 0.2% |
| Butylparaben | 0.2% |
| Ethylparaben | 0.2% |
| Propylparaben | 0.2% |
| Triethanolamine | 0.2% |

EXAMPLE 18

| Time Signature Pure Ginseng Cactus Masque | |
| --- | --- |
| Cactus (*Cereus Grandiflorus*) Fruit Extract | 27.9% |
| Ginseng (*Panax Ginseng*) Berry Extract | 20% |
| Cactus (*Cereus Grandiflorus*) Extract | 15% |
| Ginseng (*Panax Ginseng*) Root Extract Extract | 5% |
| SD Alcohol 40B | 3% |
| Glycerin | 3% |
| Hybrid Sunflower (*Helianthus Annuus*) Oil | 2% |
| Polyacrylamide | 2% |
| C13–14 Isoparaffin | 2% |
| Laureth-7 | 2% |
| Cyclomethicone | 2% |
| Avocado (*Persea Gratissima*) | 2% |
| Cucumber (*Cucumis Sativus*) | 2% |
| Jasmine (*Jasminum Officinale*) | 2% |
| Orange (*Citrus Aurantium Dulcis*) Peel | 2% |
| Flowery Knotweed (*Polygonum Aviculare*) | 1% |
| Hibiscus Sabdariff | 1% |
| Mulberry (*Morus Alba*) Leaf | 1% |
| Riboflavin (Vitamin B2) | 1% |
| Tocopheryl Acetate (Vitamin E Acetate) | 1% |
| Niacin (Vitamin B3) | 1% |
| Pantothenic Acid (Provitamin B5) | 1% |
| Disodium Edta | 0.1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 19

| Replenishing Masque for Normal Skin | |
| --- | --- |
| Ginseng (*Panax Ginseng*) Berry Extract | 2% |
| Cactus (*Cereus Grandiflorus*) | 3% |
| Cactus (*Cereus Grandiflorus*) Fruit | 5% |
| Water | 39.9% |
| Glycerin | 5% |
| Cyclomethicone | 5% |
| Polyacrylamide | 5% |
| C13–14 Isoparaffin | 5% |
| Laureth-7 | 5% |
| Aluminum Starch Octenylsuccinate | 5% |
| Hybrid Sunflower (*Helianthus Annuus*) Oil | 5% |
| Grape (*Vitis Vinifera*) Seed Extract | 2% |

-continued

Replenishing Masque for Normal Skin

| | |
|---|---|
| Ginseng (*Panax Ginseng*) Root Extract | 1% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Flowery Knotweed (*Polygonum Aviculare*) | 1% |
| Hibiscus Sabdariff | 1% |
| Mulberry (Morus Alba) Leaf | 1% |
| Riboflavin (Vitamin B2) | 1% |
| Tocopheryl Acetate (Vitamin E Acetate) | 1% |
| Niacin (Vitamin B3) | 1% |
| Pantothenic Acid (Provitamin B5) | 1% |
| Disodium Edta | 0.1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 20

Deep Purifying Clay Masque

| | |
|---|---|
| Ginseng (*Panax Ginseng*) Berry Extract | 1% |
| Cactus (*Cereus Grandiflorus*) | 3% |
| Cactus (*Cereus Grandiflorus*) Fruit | 2.5% |
| Water | 57.5% |
| Kaolin | 7% |
| Glycerin | 5% |
| Glyceryl Stearate SE | 5% |
| Bentonite | 3% |
| Ginseng (*Panax Ginseng*) Root Extract | 3% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Flowery Knotweed (*Polygonum Aviculare*) | 1% |
| Hibiscus Sabdariff | 1% |
| Mulberry (*Morus Alba*) Leaf | 1% |
| Riboflavin (Vitamin B2) | 1% |
| Tocopheryl Acetate (Vitamin E Acetate) | 1% |
| Niacin (Vitamin B3) | 1% |
| Pantothenic Acid (Provitamin B5) | 1% |
| Magnesium Aluminum Silicate | 1% |
| Phenoxyethanol | 0.2% |
| Methylparaben | 0.2% |
| Ethylparaben | 0.2% |
| Propylparaben | 0.2% |
| Disodium Edta | 0.2% |

EXAMPLE 21

Advanced Spot Control

| | |
|---|---|
| Ginseng (*Panax Ginseng*) Berry Extract | 5% |
| Cactus (*Cereus Grandiflorus*) | 1% |
| Cactus (*Cereus Grandiflorus*) Fruit | 5% |
| Water | 61.4% |
| SD Alcohol 40B | 7% |
| Glycerin | 5% |
| Grape (*Vitis Vinifera*) Seed Extract | 2% |
| Ginseng (*Panax Ginseng*) Root Extract | 2% |
| Chrysanthemum Coccineum | 1% |
| Cucumber (*Cucumis Sativus*) | 1% |
| Sage (*Salvia Officinalis*) | 1% |
| Grapefruit (*Citrus Grandis*) Peel | 1% |
| Kiwi (*Actinidia Chinensis*) | 1% |

-continued

Advanced Spot Control

| | |
|---|---|
| Lemon (*Citrus Medica Limonum*) | 1% |
| Orange (*Citrus Aurantium Dulcis*) Peel | 1% |
| Niacin (Vitamin B3) | 1% |
| Folic Acid | 1% |
| Tocopheryl Acetate (Vitamin E Acetate) | 1% |
| Triclosan | 1% |
| Carbomer | 0.3% |
| Triethanolamine | 0.3% |

EXAMPLE 22

Intensive Day Defense

| | |
|---|---|
| Ginseng (*Panax Ginseng*) Berry Extract | 2% |
| Cactus (*Cereus Grandiflorus*) | 1% |
| Cactus (*Cereus Grandiflorus*) Fruit | 2% |
| Octyl Methoxycinnamate | 2% |
| Oxybenzone | 2% |
| Avobenzone | 2% |
| Phenylbenzimidazole Sulfonic Acid | 2% |
| Water | 45.5% |
| Aloe Barbadensis Gel | 4% |
| Glycerin | 4% |
| Octyl Stearate | 3% |
| C12–15 Alkyl Bezoate | 3% |
| Stearic Acid | 3% |
| Glyceryl Stearate | 3% |
| Isopropyl Palmitate | 2.5% |
| Octocrylene | 2% |
| Sodium Stearoyl Lactylate | 2% |
| Grape (*Vitis Vinifera*) Seed Extract | 2% |
| Ginseng (*Panax Ginseng*) Root Extract | 2% |
| Avocado (*Persea Gratissima*) | 1% |
| Cucumber (*Cucumis Sativus*) | 1% |
| Jasmine (*Jasminum Officinale*) | 1% |
| Pyridoxine (Vitamin B6) | 1% |
| Riboflavin (Vitamin B2) | 1% |
| Tocopheryl Acetate (Vitamin E Acetate) | 1% |
| Ascorbic Acid (Vitamin C) | 1% |
| Niacin (Vitamin B3) | 1% |
| Triethanolamine | 1% |
| Potassium Hydroxide | 1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 23

Body Wash

| | |
|---|---|
| Ginseng (*Panax Ginseng*) Berry Extract | 3% |
| Cactus (*Cereus Grandiflorus*) | 3% |
| Cactus (*Cereus Grandiflorus*) Fruit | 3% |
| Water | 52% |
| Decyl Glucoside | 6% |
| Aloe Barbadensis Gel | 6% |
| PEG-120 Methyl Glucose Dioleate | 6% |
| Ammonium Laureth Sulfate | 5% |
| Disodium Cocoamphodiacetate | 4% |
| Grape (*Vitis Vinifera*) Seed Extract | 1% |
| Chrysanthemum Coccineum | 1% |
| Cucumber (*Cucumis Sativus*) Sage | 1% |
| Kiwi (*Actinidia Chinensis*) | 1% |
| Lemon (*Citrus Medica Limonum*) | 1% |
| Rose (*Rosa Damascena*) | 1% |

-continued

| Body Wash | |
|---|---|
| White Water Lily (*Nymphaea Alba*) | 1% |
| Riboflavin (Vitamin B2) | 1% |
| Tocopheryl Acetate (Vitamin E Acetate) | 1% |
| PEG-7 Glyceryl Cocoate | 1% |
| Cocamidopropyl Betaine | 1% |
| Fragrance | 0.2% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 24

| Hydrating Exfoliant | |
|---|---|
| Ginseng (*Panax Ginseng*) Berry Extract | 2% |
| Cactus (*Cereus Grandiflorus*) | 3% |
| Cactus (*Cereus Grandiflorus*) Fruit | 4% |
| Water | 44.5% |
| Disodium Laureth Sulfosuccinate | 6% |
| Polyethylene | 5% |
| Glycerin | 5% |
| Cocamidopropyl Betaine | 4.5% |
| PEG-120 Methyl Glucose Dioleate | 4% |
| Triethanolamine | 4% |
| Ginseng (*Panax Ginseng*) Root Extract | 3% |
| Grape (*Vitis Vinifera*) Seed Extract | 2% |
| Chrysanthemum Coccineum | 1% |
| Cucumber (*Cucumis Sativus*) | 1% |
| Sage (*Salvia Officinalis*) | 1% |
| Grapefruit (*Citrus Grandis*) Peel | 1% |
| Kiwi (*Actinidia Chinensis*) | 1% |
| Lemon (*Citrus Medica Limonum*) | 1% |
| Rose (*Rosa Damascena*) | 1% |
| Algae | 1% |
| White Water Lily (*Nymphaea Alba*) | 1% |
| Niacin (Vitamin B3) | 1% |
| Tocopheryl Acetate (Vitamin E Acetate) | 1% |
| Polysorbate 20 | 1% |
| Benzophenone-4 | 0.2% |
| Phenoxyethanol | 0.2% |
| Methylparaben | 0.2% |
| Butylparaben | 0.2% |
| Ethylparaben | 0.2% |
| Propylparaben | 0.2% |
| Carbomer | 0.2% |
| Disodium Edta | 0.2% |

EXAMPLE 25

| Hair Conditioner | |
|---|---|
| Ginseng (*Panax Ginseng*) Berry Extract | 6% |
| Cactus (*Cereus Grandiflorus*) | 6% |
| Cactus (*Cereus Grandiflorus*) Fruit | 6% |
| Water | 52% |
| Isopropyl Palmitate | 6% |
| Behentrimonium Methosulfate | 6% |
| Grape (*Vitis Vinifera*) Seed Extract | 3% |
| Avocado (*Persea Gratissima*) | 1% |
| Cucumber (*Cucumis Sativus*) | 1% |
| Jasmine (*Jasminum Officinale*) | 1% |
| Orange (*Citrus Aurantium Dulcis*) Peel | 1% |
| Chrysanthemum Coccineum | 1% |
| Pantothenic Acid (Provitamin B5) | 1% |
| Phytantriol | 1% |

-continued

| Hair Conditioner | |
|---|---|
| Folic Acid | 1% |
| Biotin (Vitamin H) | 1% |
| PG-Hydroxyethylcellulose Cocodimonium Chloride | 1% |
| Tridecyl Stearate | 1% |
| Neopentyl Glycol Disaprylate | 1% |
| Tridecyl Trimellitate | 1% |
| Silk Amino Acids | 1% |
| Phenoxyethanol | 0.2% |
| Methylparaben | 0.2% |
| Butylparaben | 0.2% |
| Ethylparaben | 0.2% |
| Propylparaben | 0.2% |

EXAMPLE 26

| All-Day Hydrating Nourisher for Oily Skin | |
|---|---|
| Ginseng (*Panax Ginseng*) Berry Extract | 4% |
| Cactus (*Cereus Grandiflorus*) | 2% |
| Cactus (*Cereus Grandiflorus*) Fruit | 4% |
| Water | 52.8% |
| Glycerin | 5% |
| Cyclomethicone | 5% |
| Polyacrylamide | 4% |
| C13–14 Isoparaffin | 4% |
| Laureth-7 | 4% |
| Grape (*Vitis Vinifera*) Seed Extract | 2% |
| Ginseng (*Panax Ginseng*) Root Extract | 2% |
| Avocado (*Persea Gratissima*) | 1% |
| Cucumber (*Cucumis Sativus*) | 1% |
| Jasmine (Jasminum Officinale) | 1% |
| Orange (*Citrus Aurantium Dulcis*) Peel | 1% |
| Flowery Knotweed (*Polygonum Aviculare*) | 1% |
| Hibiscus Sabdariff | 1% |
| Tocopheryl Acetate (Vitamin E Acetate) | 1% |
| Ascorbic Acid (Vitamin C) | 1% |
| Folic Acid | 1% |
| Acrylates Copolymer | 0.5% |
| Isopropyl Palmitate | 0.5% |
| Disodium Edta | 0.2% |
| Phenoxyethanol | 0.2% |
| Methylparaben | 0.2% |
| Butlyparaben | 0.2% |
| Ethylparaben | 0.2% |
| Propylparaben | 0.2% |
| Carbomer | 0.2% |
| Triethanolamine | 0.2% |

EXAMPLE 27

| Time Signature, Cactus Ginseng Essence | |
|---|---|
| Cactus (*Cereus Grandiflorus*) Fruit Extract | 45.3% |
| Ginseng (*Panax Ginseng*) Berry Extract | 15% |
| Cactus (*Cereus Grandiflorus*) Extract | 5% |
| Ginseng (*Panax Ginseng*) Root Extract | 3% |
| Grape (*Vitis Vinifera*) Seed Extract | 3% |
| Shea Butter (*Butyrospermum Parkii*) | 3% |
| Glycerin | 3% |
| Cyclomethicone | 3% |
| Isopropyl Palmitate | 2% |
| Glyceryl Stearate | 2% |
| Stearic Acid | 2% |
| Sodium Behenoyl Lactylate | 1% |
| Avocado (*Persea Gratissima*) | 1% |
| Cucumber (*Cucumis Sativus*) | 1% |
| Jasmine (*Jasminum Officinale*) | 1% |

-continued

| Time Signature, Cactus Ginseng Essence | |
|---|---|
| Orange (*Citrus Aurantium Dulcis*) Peel | 1% |
| Flowery Knotweed (*Polygonum Aviculare*) | 1% |
| Hibiscus Sabdariff | 1% |
| Mulberry (*Morus Alba*) Leaf | 1% |
| Pyridoxine (vitamin B6) | 1% |
| Riboflavin (Vitamin B2) | 1% |
| Tocopheryl Acetate (Vitamin E Acetate) | 1% |
| Pantothenic Acid (Provitamin B5) | 1% |
| Xanthan Gum | 0.3% |
| Carbomer | 0.3% |
| Disodium Edta | 0.1% |
| Phenoxyethanol | 0.2% |
| Methylparaben | 0.2% |
| Butlyparaben | 0.2% |
| Ethylparaben | 0.2% |
| Propylparaben | 0.2% |
| Triethanolamine | 0.2% |

EXAMPLE 28

| Tooth Paste: | |
|---|---|
| Ginseng (*Panax Ginseng*) Berry Extract | 3% |
| Cactus (*Cereus Grandiflorus*) Fruit | 3% |
| Stevia | 25% |
| Deionized Water | 21.6% |
| Hydrated Silica | 20% |
| Sorbitol | 18% |
| Ginseng (*Panax Ginseng*) Root Extract | 4% |
| Sodium Lauroyl Sarcosinate | 1.5% |
| Flavor | 1% |
| PEG-6 | 0.8% |
| Tetrasodium Pyrophosphate | 0.5% |
| Cellulose gum | 0.5% |
| Sodium Benzoate | 0.5% |
| Triclosan | 0.3% |
| Hydrogen Peroxide | 0.3% of 35% actives |

What is claimed is:

1. A topical skin care composition consisting essentially of: ginseng berry extract, water, SD alcohol 40 B, glycerin, grape seed extract, ginseng root extract, chrysanthemum coccineum extract, cucumber extract, sage, grapefruit peel, kiwi, lemon, orange peel, neacin, folic acid, tocoopheryl acetate, triclosan, carbomer, and triethanolamine.

2. A method of treating skin through application of a topical preparation, comprising the steps of:

a) providing a ginseng berry extract, wherein the ginseng berry extract is extracted by:
 i) crushing whole ginseng berries, thereby separating a juice portion of the berries from a seed portion of the berries; and
 ii) removing the seed portion from the juice portion by filtration; and b) applying the ginseng berry extract to the skin.

3. The method of claim 2, further comprising the step of blending the ginseng berry extract with an herbal ingredient prior to applying the ginseng berry extract to the skin.

4. The method of claim 2, further comprising the step of blending the ginseng berry extract with ginseng root prior to applying the ginseng berry extract to the skin.

5. The method of claim 2, further comprising the step of blending the ginseng berry extract with a facial cleanser composition prior to applying the ginseng berry extract to the skin.

6. The method of claim 2, further comprising the step of blending the ginseng berry extract with a body wash composition prior to applying the ginseng berry extract to the skin.

7. The method of claim 2, further comprising the step of blending the ginseng berry extract with a shampoo prior to applying the ginseng berry extract to the skin.

8. The method of claim 2, wherein filtration is through a course screen filter.

9. The method of claim 2, wherein the whole ginseng berries are crushed in a press.

* * * * *